US011559612B2

United States Patent
Beniash et al.

(10) Patent No.: US 11,559,612 B2
(45) Date of Patent: *Jan. 24, 2023

(54) USE OF SELF-ASSEMBLED ALKYLSILANE COATINGS FOR DRUG DELIVERY APPLICATIONS

(71) Applicant: UNIVERSITY OF PITTSBURGH—OF THE COMMONWEALTH SYSTEM OF HIGHER EDUCATION, Pittsburgh, PA (US)

(72) Inventors: Elia Beniash, Pittsburgh, PA (US); Avinash Patil, Pittsburgh, PA (US)

(73) Assignee: UNIVERSITY OF PITTSBURGH —OF THE COMMONWEALTH SYSTEM OF HIGHER EDUCATION, Pittsburgh, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/634,186

(22) PCT Filed: Jul. 30, 2018

(86) PCT No.: PCT/US2018/044307
§ 371 (c)(1),
(2) Date: Jan. 27, 2020

(87) PCT Pub. No.: WO2019/023694
PCT Pub. Date: Jan. 31, 2019

(65) Prior Publication Data
US 2020/0384164 A1   Dec. 10, 2020

Related U.S. Application Data

(60) Provisional application No. 62/538,127, filed on Jul. 28, 2017.

(51) Int. Cl.
| A61L 31/16 | (2006.01) |
| A61K 31/352 | (2006.01) |
| A61K 31/65 | (2006.01) |
| A61L 31/14 | (2006.01) |
| A61L 29/14 | (2006.01) |
| A61L 29/16 | (2006.01) |

(52) U.S. Cl.
CPC ............ *A61L 31/16* (2013.01); *A61K 31/352* (2013.01); *A61K 31/65* (2013.01); *A61L 29/148* (2013.01); *A61L 29/16* (2013.01); *A61L 31/148* (2013.01)

(58) Field of Classification Search
None
See application file for complete search history.

(56) References Cited

U.S. PATENT DOCUMENTS

| 5,356,433 A | 10/1994 | Rowland et al. |
| 8,834,913 B2 | 9/2014 | Shaw et al. |
| 2009/0018639 A1 | 1/2009 | Kuehling |
| 2009/0123516 A1* | 5/2009 | Agrawal ............... B82Y 40/00 514/1.1 |
| 2009/0258049 A1 | 10/2009 | Klein et al. |
| 2011/0236432 A1* | 9/2011 | Majd ..................... A61L 27/34 424/400 |

FOREIGN PATENT DOCUMENTS

WO    WO-2006108065 A2 * 10/2006 ........... B23K 26/382

OTHER PUBLICATIONS

Liu, ACS Applied Materials & Interfaces, 8, 2016 (Year: 2016).*
Liu, Acta Biomaterialia, 9, 2013 (Year: 2013).*
Shimojima, Langmuir, 18, 2002 (Year: 2002).*
Liu et al., Enhanced in Vitro and in Vivo Performance of Mg—Zn—Y—Nd Alloy Achieved with APTES Pretreatment for Drug-Eluting Vascular Stent Application, ACS Applied Materials & Interfaces (Jun. 22, 2016), 8:17842-17858.
Patil et al., Anticorrosive Self-Assembled Hybrid Alkylsilane Coatings for Resorbable Magnesium Metal Devices, ACS Biomaterials Science & Engineering (Feb. 24, 2017), 3:518-529.
International Search Report and Written Opinion for PCT/US2018/044307, dated Oct. 16, 2018.

* cited by examiner

*Primary Examiner* — Robert A Wax
*Assistant Examiner* — William Craigo
(74) *Attorney, Agent, or Firm* — Carol A. Marmo; Eckert Seamans Cherin & Mellott, LLC

(57) ABSTRACT

The invention relates to self-assembled organosilane- and small molecule drug-containing coatings for resorbable medical implant devices. The coatings can be prepared from precursor compositions containing an organosilane and a small molecule drug, and can be applied to substrates. Prior to applying the coatings, the surfaces of the substrates can be pretreated. The coatings can be functionalized with a binding compound that is coupled with an active component. The coatings can be applied using various techniques and apparatus, more particularly, by a deep-coating process conducted at ambient conditions.

11 Claims, 1 Drawing Sheet

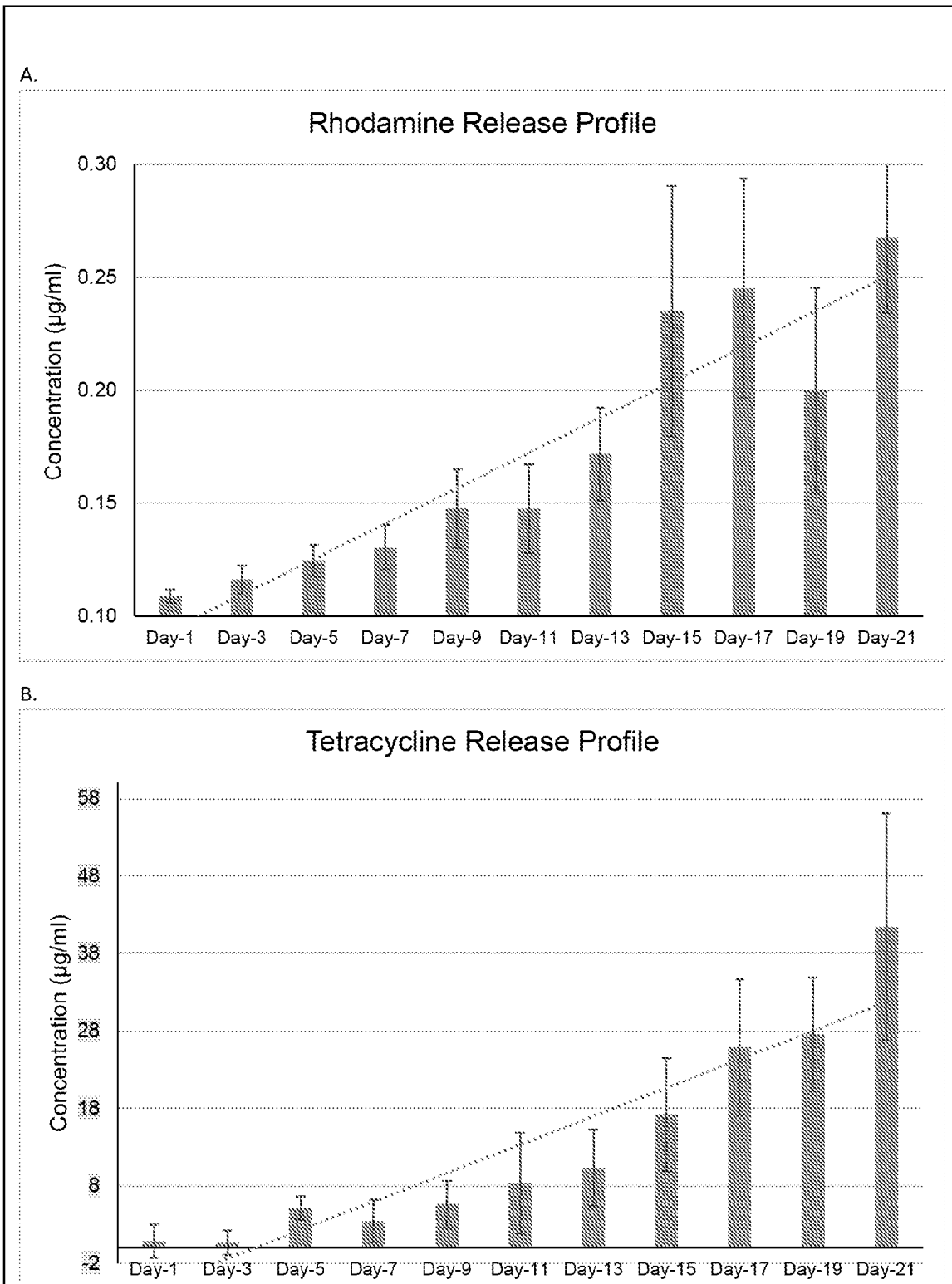

USE OF SELF-ASSEMBLED ALKYLSILANE COATINGS FOR DRUG DELIVERY APPLICATIONS

CROSS-REFERENCE TO RELATED APPLICATIONS

This application is a U.S. National Stage Application under 35 U.S.C. § 371 of International Patent Application No. PCT/US2018/044307, filed on Jul. 30, 2018, entitled USE OF SELF-ASSEMBLED ALKYLSILANE COATINGS FOR DRUG DELIVERY APPLICATIONS", which claims priority under 35 U.S.C. § 119(e) to U.S. Provisional Patent Application Ser. No. 62/538,127, filed Jul. 28, 2017, entitled "USE OF SELF-ASSEMBLED ALKYLSILANE COATINGS FOR DRUG DELIVERY APPLICATIONS", which are herein incorporated by reference.

GOVERNMENT SUPPORT

This invention was made with government support under EEC0812348 awarded by the National Science Foundation. The government has certain rights in the invention.

FIELD OF THE INVENTION

The present invention relates to organosilane-containing compositions that contain small molecule drugs, methods of preparing the compositions, methods of depositing/applying the compositions on a substrate to form a self-assembled organosilane-containing coating, and uses for the coated substrates as medical implant devices and for drug delivery systems. More particularly, the present invention relates to the addition of small molecule drugs to reaction mixtures prior to their deposition/application on substrates to form coatings. The small molecule drugs are present in the resultant self-assembled organosilane-containing coatings formed on the substrates, and they are released therefrom into a patient body. The release of the small molecule drugs can be over an extended period of time, such as, multiple days or weeks.

BACKGROUND OF THE INVENTION

Every year millions of orthopedic and craniofacial surgical procedures are performed in the United States, which require placement of metal, e.g., stainless steel or titanium, hardware in a patient body. After bone healing is complete, these metal implant devices are no longer needed. The devices can be left in sit or, alternatively, they can be removed. Each of these alternatives has disadvantages or problems associated therewith. For example, leaving the hardware in situ increases the chances of infection and rejection, and removal of the hardware requires a second surgery and causes a risk of infection, pain and discomfort to the patient, as well as it being an additional expense. To overcome these disadvantages or problems, there has been developed a number of resorbable polymeric devices that are effective to degrade over a period of time. Thus, the device does not remain in-situ and there is no need to surgically removing the device because when the device is no longer needed, the polymeric material degrades or dissolves within the patient body. However, there are also disadvantages associated with the resorbable polymer devices. For instance, it has been found that the resorbable polymeric materials, which are used for the construction of biodegradable medical implant devices, can lack mechanical strength as compared to that exhibited by metal implants and have a limited set of applications. As a result, there is an interest in the art to identify materials that degrade over time while demonstrating sufficient mechanical strength prior to degradation.

It has been found that the development of new technologies for implantable devices based on resorbable magnesium and magnesium alloys has the potential to make a significant clinical impact. Magnesium and magnesium alloys are suitable materials for the construction of resorbable devices because they have mechanical properties compatible to bone and can be resorbed over a period of time. However, there are other properties of magnesium and magnesium alloys that are problematic for their use as medical implant devices. For example, magnesium is not typically used in the fabrication of medical implant devices primarily because the corrosion of magnesium results in the production of hydrogen. Medical implant devices constructed of magnesium can cause the accumulation of hydrogen in areas surrounding the device and thus, result in the formation of gas cavities in the patient body. In order for magnesium and magnesium alloys to be considered as suitable materials for use in constructing medical implant devices, the rate of corrosion of these materials needs to be closely monitored and controlled to prevent formation of gas cavities. Thus, there are a number of relevant characteristics that have to be controlled in order to achieve the best clinical outcomes including, for example, rate of resorption, control of corrosion products, tissue integration and osteoconduction properties of the device.

It is known to deposit a coating composition on the surface of metal implant devices to modify the properties, e.g., corrosion, of the devices. Coatings for metal-based implants have been classified as conversion or deposition coatings. Conversion coatings are generally formed in situ through a reaction between the substrate and its environment, and are typically inorganic. For application to magnesium or magnesium alloys, these coatings are often composed of oxides, phosphates or fluorides. Conversion coatings typically, advantageously, exhibit good adhesion to the substrate. However, there are disadvantages associated with mechanical durability and biocompatibility of the conversion coatings. Deposition coatings are typically organic or ceramic and are applied through physical interactions with the surface of a metal substrate. For application to magnesium or magnesium alloy substrates, deposition coatings often require a conversion coating pre-treatment to improve adhesion to the alloy substrates. In the absence of a conversion coating pre-treatment, e.g., one-step deposition coatings, it is likely that the coated substrate will demonstrate poor adhesion and corrosion protection.

There is a desire in the art to develop a mechanism for controlling the rates of corrosion of magnesium and magnesium alloy in order to reduce or minimize the production and accumulation of hydrogen resulting therefrom, and to construct medical implant devices from materials that demonstrate sufficient mechanical strength when needed and degradation over time when no longer needed.

Further, there is a desire to develop coatings that are effective to control rates of corrosion of magnesium and magnesium alloy, and to reduce or minimize the production and accumulation of hydrogen resulting therefrom, and that demonstrate good adherence or adhesion to the magnesium and magnesium alloy.

Furthermore, there is a desire to incorporate drugs, e.g., small molecule organic compounds, into the coating compositions and resultant self-assembled organosilane-containing coatings such that the coated substrates can be employed as drug release systems in the patient body. It is particularly advantageous for the drugs to be released over a period of time, such as, an extended time period of several days or several weeks.

SUMMARY OF THE INVENTION

An object of the present invention is to develop novel coating compositions for application to substrates for use as medical implant devices. In particular, an object of the present invention is to develop hybrid bio-inspired anticorrosive coatings based on self-assembled multilayer organosilane, wherein the coatings include small molecule organic compounds that are effective as a drug release system over a period of time. The small molecule organic compounds can be added to reaction mixtures, e.g., coating compositions, prior to deposition/application of the coatings on the substrates. Following deposition/application of the self-assembled organosilane-containing coatings and subsequent implantation of the medical implant devices, the small molecule organic compounds may be released from the coatings according to an extended release profile, e.g., as the coatings degrade on the corroding substrate in the body, to provide a drug delivery system.

Further, the surface of these coatings can be modified via covalent bonding with an active component, including bioactive molecules, such as proteins and peptides. These surface chemistry modifications can provide the ability to control different physical chemical properties of the coatings, including but not limited to, hydrophobicity and charge, as well as bioactivity. Thus, the coatings can effectively control the degradation rate of magnesium and magnesium alloy resorbable devices to insure safety and efficiency, and to induce desirable tissue responses. Further, these coatings can be functionalized to regulate the rate of corrosion and insure the device integration into target tissues.

In one aspect, the invention provides a coated substrate that includes an uncoated substrate having an outer surface, and a self-assembled organosilane-containing coating deposited on the outer surface. The coating includes organosilane and small molecule drug.

The small molecule drug can be selected from a wide variety of small molecule drugs known in the art, such as, anti-inflammatory drugs, antibiotic drugs, antibacterial drugs, and mixtures or combinations thereof. In certain embodiments, the small molecule drug is selected from steroid, rapamycin, Metronidazole, erythromycin, tetracycline, and mixtures and combinations thereof.

The organosilane can include alkyltriethoxysilane. The alkyltriethoxysilane may have a tail including $C_4$-$C_{20}$ aliphatic backbone and a silane head. In certain embodiments, the organosilane includes a copolymer of decyltriethoxysilane and tetramethoxysilane.

The substrate may be composed of a material selected from magnesium, magnesium alloy, and other material known to corrode in the body of a patient.

The coated substrate can also include a binding compound on the surface of the coating, and an active component coupled to the binding compound. The binding compound can be selected from amine, carboxyl, thiol, hydroxyl, and mixtures and combinations thereof. In certain embodiments, the binding compound is 3-aminopropyl-trimethoxysilane.

The coated substrate may have a pretreatment applied directly to the outer surface of the substrate, wherein the pretreatment underlies the coating. The pretreatment may be selected from a nitric acid polish, nitric acid etch, mechanical polishing, sodium hydroxide passivation, and combinations thereof.

The coating deposited on the substrate can be in the form of a pattern.

The binding compound can be coupled to a surface of the coating or mixed with the composition that forms the coating.

In another aspect, the invention provides a method of preparing a drug delivery system. The method includes obtaining an uncoated substrate having an outer surface; preparing a precursor composition including combining an organosilane and a small molecule drug; applying the precursor composition to the uncoated substrate to form a coated substrate; implanting the coated substrate in a patient body; and releasing the small molecule drug in the patient body.

The substrate can include magnesium, and the magnesium may degrade within the patient body.

BRIEF DESCRIPTION OF THE DRAWINGS

FIG. 1 contains two bar graphs, A and B, showing rhodamine (A) and tetracycline (B) release profiles from alkylsilane-coated magnesium discs.

DETAILED DESCRIPTION OF THE INVENTION

The invention relates to medical implant devices, organosilane- and small molecule drug-containing compositions, self-assembled organosilane- and small molecule drug-containing coatings, coated medical implant devices, methods of preparing and applying/depositing the coatings, and drug delivery systems. The small molecule drug, e.g., organic compound, is incorporated into a reaction mixture prior to the applying/depositing step. Following application of the coating on a substrate to form a coated article, and implantation of the coated article in a patient body, the small molecule drug is released from the coating over a period of time, such that there is provided an extended release, drug delivery system in conjunction with the implant device. The drug is released as the self-assembled coating degrades on the corroding metal or metal alloy surface of the implant device.

As used in here, the term "small molecule" refers to a low molecular weight molecule or organic compound. Most drugs are small molecules. In certain embodiments, the small molecule can have a molecular weight of less than 1,000 Daltons or, in some instances, less than 500 Daltons. Furthermore, in certain embodiments, the small molecule has a size of approximately 1 nm.

The medical implant devices can be composed of a wide variety of materials that are known in the art for such purposes. In general, the substrate of the invention includes a material that is known to corrode in the body of a patient. Non-limiting examples of suitable substrates include ceramic, polymer, metal, metal alloy, and mixtures and combinations thereof. In certain embodiments, the substrate is selected in accordance with the objectives of controlling the rates of corrosion, in order to reduce or minimize the production and accumulation of hydrogen resulting therefrom, and to construct medical implant devices from materials that demonstrate sufficient mechanical strength when needed and degradation over time when no longer needed.

In certain embodiments, the substrate is composed of magnesium or magnesium alloy in accordance with satisfying these objectives.

The substrate may be selected from a wide variety of biodegradable materials. Non limiting examples include, but are not limited to, those compositions described in PCT Application having International Application No. PCT/US2012/058939 entitled "Biodegradable Metal Alloys" filed on Oct. 5, 2012 and based on U.S. Provisional Patent Application 61/544,127 entitled "Biodegradable Metal Alloys" filed on Oct. 6, 2011, which are incorporated in their entirety herein by reference.

In certain embodiments, the substrate used in the invention is composed of magnesium alloy including elemental magnesium and one or more other elemental metal components, such as, but not limited to, iron, zirconium, manganese, calcium, yttrium and zinc. Optionally, other elemental metals may be present, such as, aluminum. The amount of each of the components can vary and, in general, the amounts are selected such that the resulting magnesium alloys are within acceptable non-toxic limits, sufficiently biocompatible and degradable over a period of time.

The self-assembled coatings include organosilane, e.g., hybrid organosilanes. The organosilane self-assembles into a multi-layered structure. In certain embodiments, the organosilane includes amphyphilic organosilane having an aliphatic tail containing a backbone of 4 to 20 carbon atoms (i.e., $C_4$ to $C_{20}$) and a silane head. Non-limiting examples of suitable organosilanes include alkylsilanes. In certain embodiments, the coatings include alkyltrialkoxysilane, such as, but not limited to, decyltriethoxysilane. The alkylsilane including alkyltrialkoxysilane, e.g., decyltriethoxysilane, can be co-polymerized with another polymer component, such as, but not limited to, tetramethoxysilane (TMOS). Further, in certain embodiments, the alkylsilane, e.g., alkyltrialkoxysilane, co-polymer is combined with a crosslinking material, such as, but not limited to, a UV crosslinking agent. For example, a precursor solution may be prepared by combining decyltriethoxysilane, TMOS and alcohol, such as ethanol.

As previously described herein, the coating compositions, e.g., precursor solutions, also include a small molecule drug. The small molecule drug can be selected from a wide variety of small molecule drugs known in the art, such as, anti-inflammatory drugs, antibiotic drugs, antibacterial drugs and mixtures or combinations thereof. In certain embodiments, the anti-inflammatory drugs include steroids and rapamycin, and the antibiotic drugs include metronidazole, erythromycin and tetracyclin. It is understood that these are non-limiting examples of suitable small molecule drugs, but the invention is not limited to these particular drugs. In certain embodiments, one or more small molecule drugs can be added to the precursor solution. Addition of the small molecule drug(s) to the precursor solution can vary. In an embodiment, alkylsilane is co-polymerized with another polymer and hydrolyzed with, for example, sodium hydroxide. The small molecule drug is then added to the hydrolyzed solution. For example, one or more of an anti-inflammatory drug and/or an antibiotic drug may be added to a hydrolyzed precursor solution.

The coating composition with the small molecule drug is deposited on or applied to a substrate, such as a magnesium or magnesium alloy substrate, to form a coating and the small molecule drug is released as the coating degrades. The drug release is facilitated by degradation of the coating. Degradation of the coating is induced by corrosion of the underlying substrate, e.g., magnesium or magnesium alloy substrate. By regulating corrosion, e.g., rate of corrosion, coating degradation can be controlled and in turn release, e.g., rate of release, of the small molecule drug can be controlled. In a comparison of a glass substrate and a magnesium alloy substrate, which were each coated with a solution containing alkylsilane and tetracyclin, the inventors found that release of tetracyclin was not observed for the alkysilane-coated glass substrate; however, tetracyclin release was observed for the degraded coated magnesium alloy substrate.

In general, self-assembled coatings, e.g., monolayers or multilayers, are thin films produced by deposition of materials, such as, organosilanes. For example, alkylsilanes self-assemble into multilayered structures with alternating layers including polysiloxane and alkyl. The coatings are formed, e.g., spontaneously, on surfaces of a substrate by adsorption and include a head group, tail and functional end groups. The head group can be in a vapor phase or a liquid phase. The head group assembles onto the substrate, while the tail group organizes and assembles farther from the surface of the substrate. The substrate and head group are selected to react with each other. In certain embodiments, a hydrophilic end (e.g., head group) may bond with the substrate surface while a hydrophobic end may be opposite the hydrophilic end.

In general, the self-assembled organosilane coatings can be applied or deposited onto the substrate surfaces, e.g., of the medical implant devices, using known apparatus and conventional coating techniques. Conventional apparatus and techniques are generally known for applying/depositing a silane coating composition onto a substrate. For example, amphiphilic organosilanes form nanostructured films for glass coating applications, and organosilanes for corrosion control applications. Non-limiting examples of conventional coating techniques include, but are not limited to, physical vapor deposition, electro-deposition or electro-less deposition, as well as spinning, dipping or spraying techniques at ambient temperature.

The coating compositions, e.g., precursor solutions, can be directly applied to or deposited on the substrate surface of the medical implant devices, i.e., in the absence of any pretreatment or pre-coating of the surface. However, for the purpose of improving the adherence and/or adhesion of the coatings to the substrate surface of the devices, it may be preferable to perform pretreatment or pre-coating of the substrate surface. The coating process in accordance with the invention can optionally include pre-treating or pre-coating the surface of the substrate prior to applying/depositing the organosilane coating thereto. The pre-treatment or pre-coating is applied to or deposited on the bare, e.g., uncoated, surface of the substrate. The pre-treatment/pre-coating step can vary and may be selected from known pretreatment compounds/compositions, techniques and processes that are employed to improve adherence or adhesion of a coating to the surface of a substrate. Suitable non-limiting examples of pretreatment include mechanical polishing, polishing and/or etching the uncoated substrate with nitric acid, and/or passivating with sodium hydroxide to form a thin hydroxide layer. Without intending to be bound by any particular theory, it is believed that pretreating the substrate prior to applying the coating composition results in a more uniform coating having improved adhesion or adherence properties, as compared to coatings that are formed in the absence of pretreating the substrate.

Coatings for medical implant devices preferably exhibit special properties, such as, the ability to adapt to the intrinsically unstable physical and chemical environments of an implant device, as well as the ability to be functionalized with bioactive molecules. Without intending to be bound by any particular theory, it is believed that the coatings are effective to modify various properties and characteristics of the underlying substrate of the devices. For example, the coatings can be effective to control one or more of the following properties of the substrates: corrosion rate, production/accumulation of hydrogen, calcium phosphate precipitation, rate of resorption, fouling/antifouling, tissue integration and osteoconduction. In certain embodiments, the coatings can be effective to reduce or preclude the corrosion rate and, in turn, the production/accumulation of hydrogen, as well as reducing calcium phosphate formation around the device. These surface chemistry modifications can provide the ability to control different physical chemical properties of the coatings, including but not limited to, hydrophobicity and charge, as well as bioactivity. The hydrophobicity of the organosilane, e.g., alkylsilane, coatings can reduce bacteria adhesion and therefore, may be employed as antifouling coatings. Thus, the coated medical implant devices are particularly useful in various surgical applications, such as, but not limited to, dental, orthopedic, craniofacial, and cardiovascular.

In certain embodiments, the self-assembled organosilane coating is formed by employing a deep-coating process at ambient conditions. This process includes combining the organosilane, small molecule drug and solvent, e.g., water, to form a solution and applying the solution to a substrate, e.g., by dipping/immersing the substrate into a bath of the solution. The immersion can be for a time period ranging from minutes to hours and, typically includes sufficient time to allow the organosilane to bond to the substrate. The substrate may or may not be pretreated. Subsequent evaporation of the solvent by conventional methods induces the organosilane to self-assemble into micro- or nano-structures and thin film. The resulting coating, e.g., thin film, is rigid, uniform and has a thickness that can vary from about 100 nanometers to tens of micrometers. The thickness can depend on various factors including the organosilane composition components, the process conditions and the intended use of the coated substrate. In one embodiment, the coating has a thickness of about 1 um. Further, the coating, e.g., laminar structure, can include multiple layers. In certain embodiments, the coating may be composed of about 30 nm thick layers. Furthermore, the coating can be hydrophobic which may be particularly beneficial for cardiovascular applications.

In certain embodiments, following the preparation of the precursor solution and application/formation of the resultant coating on the surface of the substrate, the coating is partially, e.g., selectively, removed. The partial, e.g., selective, removal of the coating from the surface of the substrates can be selectively conducted by forming various patterns of coated and uncoated substrate. In certain areas of the pattern, the uncoated surface of the substrate is exposed and in other areas, the surface has the coating applied thereto.

Without intending to be bound by any particular theory, it is believed that the selectively removed, i.e., patterned, coatings are effective to modify various properties and characteristics of the underlying substrate of the a medical implant device. For example, a patterned coating can be effective to control or regulate one or more of the following properties of the substrate: corrosion rate, production/accumulation of hydrogen, rate of resorption, tissue integration and osteoconduction. In certain embodiments, for example, wherein the substrate is composed of magnesium or magnesium alloy, the patterned coating can be effective to reduce or preclude the corrosion rate and, in turn, the production/accumulation of hydrogen. Further, the surface of the coated portions of the substrate can include covalent bonding with different molecules, including bioactive molecules, such as proteins and peptides.

Surface chemistry modifications can provide the ability to control different physical chemical properties of the coating, including but not limited to, hydrophobicity and charge, as well as bioactivity. Furthermore, the patterned, substrate surface including coated and uncoated portions or parts can be used to control or regulate pre-selected or desired properties. The selective removal of the coating to expose portions or parts underneath, e.g., uncoated substrate, can be performed by employing various conventional techniques and apparatus known in the art. For example, selective removal of a coating can be conducted using one or more of laser ablation, ion etching and electron beam etching. In certain embodiments, the selective removal can include forming various patterns in the coating. The patterns can include a plurality of lines or grooves. The number, width and configuration of the lines or grooves can vary, and may correspond to, or depend on, a pre-determined amount of exposed uncoated surface necessary to achieve pre-selected or desired properties. Further, the pattern can be formed on one or more surfaces of the substrate. For example, wherein the substrate has upper and lower surfaces, the pattern can be formed on one or both of these surfaces.

Without intending to be bound by any particular theory, it is believed that selective removal of the coating eliminates inhibition of the corrosion in the exposed areas of the substrate and increases the rate of corrosion. By changing size, density and spatial distribution of exposed areas of the substrate, the corrosion rate of the entire substrate, e.g., medical implant device, or portions or parts thereof can be controlled or tuned.

Various removal patterns can be formed by lines, e.g., grooves, applied to the coated surface of the substrates to produce exposed areas. The density, e.g., number, of grooves in the pattern can vary. There can be a high density, e.g., high number, of grooves or a low density, e.g., low number, of grooves in the pattern. For example, a pattern can have four, 1-um wide grooves spaced apart by a distance of 100 um on a disc. Alternatively, the pattern can have five grooves and a spacing of 50 um, or eleven grooves with a spacing of 25 um on the disc. An increase in the density, e.g., number, of grooves results in an increase in the exposed area of the uncoated substrate and therefore, an increase in the rate of corrosion. A similar effect may be achieved by varying the width of the exposed areas, e.g., grooves, without changing their density. Thus, the rate of corrosion can be spatially regulated in different portions or parts, e.g., of a medical implant device, by having the density of the grooves be different for certain portions or parts. That is, the pattern for a disc can have a lesser density of grooves on the left-side portion of the disc and a greater density of grooves toward the right side portion of the disc. For example, from left to right or right to left, the spacing may decrease from about 100 um to about 25 um. Similarly, the pattern for a screw, for example, can have a lesser density of grooves at the top portion of the shaft and a greater density of grooves toward the lower portion of the shaft. From top to bottom, the spacing can decrease from 100 um to 25 um.

The coating in accordance with the invention has numerous advantages as compared to conventional coating technology, including, but not limited to, for example, tunability of corrosion and delivery of a drug. The thickness of the coating and its mechanical properties can be tuned or controlled, as well as the extended release of small molecule drugs.

Using organosilanes with UV crosslinkable groups provides the ability to increase stiffness simply by exposure to a UV source. Further, copolymerizing organosilanes with tetramethoxysilane produces liquid-like coatings having increased flexibility, which may be particularly useful for cardiovascular applications.

In certain embodiments, the surface of the coating is modified or functionalized to attach or bind, e.g., by covalent bonding, an active component, e.g., bioactive molecule, such as, protein and/or peptide, to the surface of the coating. A binding compound, such as, but not limited to amine, carboxyl, thiol, hydroxyl and mixtures thereof, can be used to bind one or more active components to the coating. In certain embodiments, the binding compound is attached to the surface of the coating. For example, a plurality of molecules containing silane groups, e.g., aminosilanes, such as, but not limited to aminopropyl-trimethoxysilane, can be covalently attached to the surface of the coating to provide chemistry for attachment of the active component, such as, but not limited to alkaline phosphatase, or for modifying hydrophobicity of the surface. In certain other embodiments, the binding compound can be permeated or encapsulated within the composition that forms the coating.

As used herein, the term "active component" and related terms refer to a molecule, compound, complex, adduct and/or composite that exhibits one or more beneficial activities, such as, therapeutic activity, diagnostic activity, biocompatibility, corrosion-resistance, and the like. Active components that exhibit a therapeutic activity can include bioactive agents, pharmaceutically active agents, drugs and the like. Non-limiting examples of bioactive agents include, but are not limited to, bone growth promoting agents, such as growth factors, drugs, proteins, antibiotics, antibodies, ligands, DNA, RNA, peptides, enzymes, vitamins, cells and the like, and combinations thereof.

In addition to incorporating a pharmaceutically active agent or drug into the reaction mixture or precursor solution, e.g., coating composition, by including a small molecule drug, a pharmaceutically active agent or drug can also be incorporated by covalently bonding the material to the coating surface on the medical implant device.

With the incorporation of a small molecule drug into the coating composition and/or the binding of one or more active components, the coatings and coated medical implant devices, can be effective to combine anti-corrosion properties, drug delivery capability and bioactive surface modifications, which can facilitate improved tissue integration, extended release drug delivery, and induced desirable biological responses.

Organosilane-coated substrates, in accordance with the invention, are generally effective for tissue regeneration and, in particular, bone regeneration, within a body of a patient. These substrates can be employed as materials of construction for various medical implant devices. Non-limiting examples of suitable medical devices include, but are not limited to, scaffolds, plates, meshes, staples, screws, pins, tacks, rods, suture anchors, tubular mesh, coils, x-ray markers, catheters, endoprostheses, pipes, shields, bolts, clips or plugs, dental implants or devices, such as but not limited to occlusive barrier membranes, graft devices, bone-fracture healing devices, bone replacement devices, join replacement devices, tissue regeneration devices, cardiovascular stents, nerve guides, surgical implants and wires.

It will be appreciated by those skilled in the art that changes could be made to the embodiments described above without departing from the broad inventive concept thereof. It is understood, therefore, that this invention is not limited to the particular embodiments disclosed and the following examples conducted, but it is intended to cover modifications that are within the spirit and scope of the invention.

Examples

1. Materials and Methods

All of the reagents used in the following experiments were purchased from Sigma Aldrich (St. Louis, Mo., USA), and were used as received unless otherwise stated.

1.1. Metal Sample Preparation

Discs, i.e., 6 mm-diameter discs, were stamped from 1 mm-thick Mg (99.9% purity) and AZ31alloy (96% Mg, 3% Al, and 1% Zn) sheets (Alfa Aesar, Ward Hill, Mass., USA), and polished with 1200 grit (5 µm) MicroCut® SiC abrasive discs (Buehler Inc., Lake Bluff, Ill., USA). The polished discs were then etched for 60 seconds in etching solution including 20 ml of 85% glycerol, 5 ml of 65% $HNO_3$ and 5 ml of glacial acetic acid. Chemical etching was done to remove debris, impurities and the oxide layer from the surface of the metal, and to smooth any scratches introduced during polishing. The etched discs were sonicated in acetone for 30 minutes and stored under vacuum until further use. Prior to deposition of the alkylsilane coating, a thin uniform hydroxide layer was formed on the discs by immersion for two hours in 3.0 M sodium hydroxide (NaOH) solution. In addition to its passivating properties, $MgOH_2$ provided means for covalent binding of silanes to the metal surface.

1.2. Synthesis and Deposition of Self-Assembled Multilayer AS Coating Encapsulating TC and Rh on Mg Self-assembled hybrid alkylsilane (AS) films on Mg were prepared using a dip-coating technique. The precursor solution was prepared by mixing 0.25 ml (0.73 mM) of n-decyl-triethoxysilane (DTEOS) (Alfa Aesar, Ward Hill, Mass., USA), 0.43 ml (2.92 mM) of tetramethoxysilane (TMOS) (Alfa Aesar, Ward Hill, Mass., USA), 2 ml (0.032 mM) of ethanol and 0.25 ml of 0.010 mM HCl (aq.). The precursor solution was stirred for 24 hours at room temperature to induce hydrolysis of DTEOS and TMOS. After 24 hours, TC (tetracycline) or Rh (used as a stand-in for a small molecule drug because it is fluorescent and can be detected by a spectrometer) was added into the hydrolyzed precursor solution at concentration of 5 mg/ml, and further stirred for 24 hours at room temperature to mix well the TC or Rh in the hydrolyzed solution. Both the solutions were kept in the dark to avoid contact with light. The Mg discs passivated with NaOH were dip coated in the TC- or Rh-containing solution for 1 minute, and dried in air for 10 minutes at room temperature in the dark. The discs were subsequently dried in an incubator at 37° C. for 24 hours to remove any trace amounts of organic solvents. The AS-coated Mg discs were stored in the dark until further use.

1.3. In Vitro Release of TC or Rh in Simulated Body Fluid (SBF)

Prior to the release study, the AS-coated Mg discs were placed in D water on an orbital shaker for 1 hour to remove any TC or Rh bound to the coated surfaces of the discs. Three disks per each group were used in the study. In-vitro release experiments were carried out in SBF at room temperature. Each disk was placed in capped test tubes containing 5 ml of SBF. Every two days, 150 µl of SBF was taken from each tube and concentrations of Tc and Rh were determined spectroscopically. The concentrations of TC or Rh were determined by measuring absorbance at 280 nm for TC, and fluorescence at excitation/emission wavelengths of 525/555 nm for Rh using a Synergy H1 microplate reader (BioTek instruments, Winooski, Vt., USA). Standard curves were created by measuring absorbance and fluorescence intensities of the series of TC and Rh samples of known concentrations. Absorbance and Fluorescence intensity of each sample was calculated as an average of three separate readings. After measurements were taken, media samples were transferred back to the corresponding tubes and capped to minimize evaporation. Cumulative release of TC or Rh over 21 day period was determined.

2.0. Results.

The release experiments demonstrated feasibility of using alkylsilane hybrid multilayered self-assembled coatings for drug release. An incremental increase in the concentration of TC and Rd in SBF media in which the alkylsilane coated Mg disks were incubated was apparent (FIG. 1). One way ANOVA analysis demonstrated that the increases in the dye concentrations for both groups were highly significant ($p=2.71219E-4$ for Rh and $p=3.41921E-5$ for TC).

We claim:

1. A partially coated medical implant device, comprising:
a magnesium or magnesium alloy substrate having an outer surface; and
a drug delivery system, comprising:
an organosilane-containing, drug-releasing coating deposited on the outer surface of the substrate such that the outer surface is only partially, selectively, covered with the coating to form portions of coated and uncoated substrate, the coating derived from a hydrolyzed precursor solution, the hydrolyzed precursor solution comprising:
an alkyltrialkoxysilane-tetramethoxy silane copolymer, comprising an amphiphilic organosilane having an aliphatic tail containing a backbone of 4 to 20 carbon atoms and a silane head, structured to self-assemble into a multi-layered structure;
an aminoalkylalkoxysilane binding compound; and
one or more small molecule drugs,
wherein the drug-releasing coating is structured to achieve an extended release of the one or more small molecule drugs into a patient body, and
wherein a rate of release of the one or more small molecule drugs is controlled by rate of degradation of the drug-releasing coating, induced by corrosion of the underlying magnesium or magnesium alloy substrate.

2. The partially coated substrate of claim 1, wherein the small molecule drug is selected from the group consisting of anti-inflammatory, antibiotic, antibacterial, and mixtures and combinations thereof.

3. The partially coated substrate of claim 2, wherein the small molecule drug is selected from the group consisting of steroids, rapamycin, Metronidazole, erythromycin, tetracycline, and mixtures and combinations thereof.

4. The partially coated substrate of claim 1, wherein the organosilane comprises alkyltriethoxysilane.

5. The partially coated substrate of claim 1, wherein the organosilane comprises a co-polymer of decyltriethoxysilane and tetramethoxysilane.

6. The partially coated substrate of claim 1, further comprising:
a binding compound on a surface of the coating; and
an active component coupled to the binding compound.

7. The partially coated substrate of claim 6, wherein the binding compound is selected from the group consisting of amine, carboxyl, thiol, hydroxyl and mixtures thereof.

8. The partially coated substrate of claim 6, wherein the binding compound comprises 3-aminopropyl-trimethoxysilane.

9. The partially coated substrate of claim 1, further comprising a pretreatment applied directly to the outer surface of the substrate, wherein the pretreatment underlies the coating.

10. The partially coated substrate of claim 9, wherein the pretreatment is selected from the group consisting of a nitric acid polish, nitric acid etch, mechanical polishing, sodium hydroxide passivation, and combinations thereof.

11. The partially coated substrate of claim 1, wherein the coating is in the form of a pattern.

* * * * *